United States Patent [19]

Kosal

[11] Patent Number: 5,504,149

[45] Date of Patent: *Apr. 2, 1996

[54] METHOD OF EMULSION POLYMERIZATION

[75] Inventor: Jeffrey A. Kosal, Midland, Mich.

[73] Assignee: Dow Corning Corporation, Midland, Mich.

[*] Notice: The term of this patent shall not extend beyond the expiration date of Pat. No. 5,502,105.

[21] Appl. No.: 296,204

[22] Filed: Aug. 25, 1994

[51] Int. Cl.$^6$ ............................................. C08L 83/00

[52] U.S. Cl. ..................... 524/837; 424/401; 424/70.1

[58] Field of Search .................. 524/837; 424/40.1, 424/70.1

[56] References Cited

U.S. PATENT DOCUMENTS 2,891,920  6/1959  Hyde et al. ............................ 260/29.2

FOREIGN PATENT DOCUMENTS 459500  12/1991  European Pat. Off. .

*Primary Examiner*—Melvyn I. Marquis
*Assistant Examiner*—Karen A. Dean
*Attorney, Agent, or Firm*—James L. DeCesare

[57] ABSTRACT

A method is described for making a silicone emulsion. According to the method, there is formed a mixture of water, a cyclic siloxane, optionally a nonionic surfactant, and a cationic surfactant. There is then added to the mixture a polymerization initiator which can be a silanolate or an organosilanolate. The mixture is heated and agitated, and the cyclic siloxane is allowed to polymerize until an emulsion is formed. The benefit of this emulsion polymerization method is that the rate of emulsion polymer formation is enhanced. Thus, the method provides for the production of emulsions in a new and more efficient manner. The silicone emulsion will produce an elastomeric product when water is removed under ambient conditions.

21 Claims, No Drawings

METHOD OF EMULSION POLYMERIZATION

BACKGROUND OF THE INVENTION

This invention is directed to a method of emulsion polymerization and to the enhancement in the rate of emulsion polymer formation. More particularly, a method is provided for the production of emulsions in a new and more efficient manner.

The problem to be solved according to this invention, is the provision of a method of making an emulsion containing a silicone polymer of a high viscosity, in a shorter period of time than is possible with techniques known in the art. Thus, standard techniques of emulsion polymerization, while effective in the production of silicone emulsions, suffer from the disadvantage of yielding suitable emulsions only after periods of time for polymerization which can often be in excess of several days. According to some standard techniques, two to five days can be required to enable the polymerization to proceed, in order that the silicone polymer in the emulsion will reach a desired high viscosity.

This time problem has been solved according to this invention, by the use of a certain unique initiator in the emulsion polymerization technique. These initiators are silanolates and organosilanolates, and the emulsions produced in accordance with the invention contain silicone polymers of equivalent or higher viscosity as standard techniques. Yet, in the present invention, the rate of emulsion polymer formation is achieved in a much shorter period of time, typically in only about three hours. In comparison to the very lengthy periods of time required for emulsion polymer formation under conditions of the standard technique, this is significant.

The silicone emulsions of the invention have been found to be especially useful as additives in the personal care market.

SUMMARY OF THE INVENTION

The invention relates to a method of making a silicone emulsion in a much shorter period of time. The emulsion is made by dispersing a siloxane in water by forming a mixture of water, a cyclic siloxane, a nonionic surfactant, and a cationic surfactant. To the mixture is added a polymerization initiator which is a silanolate or an organosilanolate. The method includes the additional steps of heating the mixture of water, cyclic siloxane, the surfactants, and the initiator; agitating the heated mixture; and allowing the cyclic siloxane to polymerize until an emulsion is formed.

In an alternate embodiment of the invention, the emulsion is made without adding a nonionic surfactant, and in that embodiment, the polymerization is conducted using only the cyclic siloxane, a cationic surfactant, and the polymerization initiator.

In yet another embodiment of the invention, silicone microemulsions are prepared according to the invention, and are formed into an elastomeric product when water is removed under ambient conditions.

The invention also relates to the use of these silicone emulsions for imparting conditioning benefits to hair.

The benefit derived from the invention is the production of an emulsion in less time by shortening the polymerization time with use of the unique initiator system.

An additional benefit obtained according to the invention is that it is now possible to produce microemulsions containing amine functional siloxanes of high viscosity, typically a viscosity in excess of about one hundred thousand Centistokes ($mm^2/s$) measured at twenty-five degrees Centigrade.

For purposes of this invention, a microemulsion is considered to be a composition in which the continuous portion of the emulsion contains a noncontinuous silicone phase which is in the form of droplets in the continuous phase of an average diameter of less than about 140 nanometers (0.140 microns). Such emulsions are particularly useful in the personal care arena for imparting conditioning benefits to hair.

These and other features, objects, advantages, and benefits, of the present invention will become more apparent from a consideration of the following detailed description thereof.

DETAILED DESCRIPTION OF THE INVENTION

Emulsions are mixtures of at least two components which are substantially immiscible in each other, and a surfactant which lowers interfacial tension between the two phases. A microscopic view of aqueous emulsions reveals two phases, an oil phase and a water phase. Depending upon the proportion of each component, the emulsion can be characterized as an oil-in-water emulsion or a water-in-oil emulsion. The chief distinction between the two being which component, the oil or water phase, comprises the continuous portion of the emulsion. The noncontinuous phase is in the form of droplets in the other phase.

Methods for making aqueous emulsions of polydiorganosiloxanes are well known in the art and can be separated into two types. Thus, emulsions can be made by mechanical means and emulsions can be made by emulsion polymerization means. Emulsions made by mechanical means typically involve homogenizing a mixture of polydiorganosiloxane, surfactant, and water using milling machinery to obtain the desired droplet sizes.

On the other hand, emulsion polymerization methods for making emulsions of high viscosity polymers involve starting with low viscosity polymer precursors, i.e., monomers, or reactive oligomers, which are immiscible in water; a surfactant to stabilize the polymer precursor droplet in water; and a water soluble polymerization catalyst. Typically, the catalyst is a strong mineral acid such as hydrochloric acid, or a strong alkaline catalyst such as sodium hydroxide. These components are added to water, the mixture is stirred, and polymerization is allowed to advance until the reaction is complete, or the desired degree of polymerization is reached and an emulsion of the polymer is formed.

One example of an emulsion polymerization process is taught in U.S. Pat. No. 2,891,920 issued Jun. 23, 1959, which shows a method of making aqueous emulsions of a polydimethylsiloxane, starting with precursor molecules of the polydimethylsiloxane. Another example of such a process is described in European Published Patent Application No. 0 459 500 A2, dated Dec. 4, 1991, which is based on a corresponding pending U.S. application Ser. No. 532,471 filed Jun. 1, 1990.

Polydiorganosiloxane precursors which can be used in the practice of the invention include cyclic siloxanes which are relatively insoluble in water, and which can be polymerized using emulsion polymerization techniques. The preferred cyclic siloxanes have the formula:

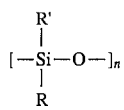

in which R and R' denote methyl, ethyl, propyl, vinyl, allyl, or phenyl; and n is 3, 4, 5, or 6. The cyclic precursors can be the pure species such as octamethylcyclotetrasiloxane, hexamethylcyclotrisiloxane, decamethylcyclopentasiloxane, tetramethyltetravinylcyclotetrasiloxane, and tetramethyltetraphenylcyclotetrasiloxane, or mixtures of the species can be used. For example, a mixture of cyclopolydimethylsiloxanes having three, four, and five siloxane units could be used.

If desired, the reaction medium can also include a small portion of other organosilicon compounds which contain a hydrolyzable or silanol group in the molecule which is capable of polymerization. Suitable compounds include for example, amine functional silanes, vinyl functional silanes, or halogenalkyl functional silanes. Representative silanes are N-(2-aminoethyl)-3-(aminopropyl)trimethoxysilane, vinyltriethoxysilane, vinyltriacetoxysilane, and 3-chloropropyltrimethoxysilane.

The polymerization medium used in the invention comprises water, an effective amount of surfactant to stabilize the polydiorganosiloxane droplets formed therein, and an effective amount of initiator to polymerize the polydiorganosiloxane precursor. The preferred amount of initiator used to catalyze the polymerization of the precursor is between 0.5 to 15 weight percent, based on the total weight of the composition depending upon the initiator employed.

The initiator used as the polymerization catalyst according to the present invention is a silanolate or an organosilanolate. These alkali-metal salts are metal derivatives of organosilanols, and have the formula $R''_x Si(OM)_{4-x}$. In the formula, R" is an alkyl radical having from one to six carbon atoms, an aryl radical, an alkenyl radical, an alkylamino radical, or an epoxy radical; and x has a value of zero to three. Suitable alkyl and aryl R" radicals are methyl, ethyl, and phenyl. Suitable alkenyl R" radicals are vinyl, allyl, propenyl, and hexenyl. Suitable aminoalkyl R" radicals are aminopropyl and ethylene diaminopropyl. Suitable epoxy R" radicals are 3-glycidoxypropyl and 2-(3,4-epoxycyclohexyl)-ethyl. M is an alkali metal in Group IA of the Periodic Table, such as lithium, sodium, potassium, rubidium, and cesium. Sodium is the preferred alkali metal. For purposes of the present invention, the value of x is preferably two or three. The most suitable initiators are sodium trimethylsilanolate $NaOSi(CH_3)_3$, sodium triphenylsilanolate $(C_6H_5)_3SiONa$, disodium dimethylsilanolate $(CH_3)_2Si(ONa)_2$, and disodiummethylaminopropylsilanolate $(CH_3)[H_2NCH_2CH_2CH_2]Si(ONa)_2$.

The sodium salts of the triorganosilanols can be obtained from the reaction of the corresponding hexaorganodisiloxane and sodium hydroxide in an alcoholic solution. Trimethylsilanolates are obtained by the reaction of hexamethyldisiloxane with sodamide or potassamide in liquid ammonia or absolute ether. Silanolates can also be obtained by the reaction of triorganoalkoxysilanes with alkali-metal hydroxides, or triorganosilanols with alkali metals or alkali-metal hydroxides.

As noted above, the mixture preferably contains a nonionic surfactant, although it may be omitted in an alternate embodiment of the invention. Most preferred for this invention is an ethoxylated fatty alcohol, although other types of nonionic emulsifiers can be employed. Such fatty alcohol ethoxylates contain in their molecule the characteristic group $-(OCH_2CH_2)_aOH$, which is attached to a fatty hydrocarbon residue of about eight to twenty carbon atoms, such as lauryl ($C_{12}$), cetyl ($C_{16}$) and stearyl ($C_{18}$). The integer "a" can have a value of one to about one hundred, but typically has a value of about 12 to 40.

Examples of commercial products found to be suitable according to the present invention, include the various polyoxyethylene fatty alcohols sold under the tradename BRIJ by ICI Americas Incorporated, of Wilmington, Del.; the tradename EMERY by the Henkel Corporation/Emery Group, of Ambler, Pa.; the trademark ETHOSPERSE® by Lonza Incorporated, of Fairlawn, N.J.; and the trademark PROMULGEN® by the Amerchol Corporation, of Edison, N.J.

A particularly preferred nonionic surfactant is BRIJ 35 Liquid. This polyoxyethylene (23) lauryl ether has an HLB value of about 16.9 and a structure corresponding to the formula $C_{12}H_{25}(OCH_2CH_2)_{23}OH$. Laureth-23 is the International Nomenclature Cosmetic Ingredient (INCI) name assigned by The Cosmetic, Toiletry, and Fragrance Association, Washington, D.C., (CTFA) to polyoxyethylene (23) lauryl ether.

Laureth-23 is also sold under the trademark AMEROXOL® LE-23 by the Amerchol Corporation, of Edison, N.J.; the tradename EMTHOX 5877 by the Henkel Corporation/Emery Group, of Ambler, Pa.; the trademark MACOL® LA-23 by PPG/Mazer of Gurnee, Ill.; and the trademark WITCONOL® 5964 by the Witco Corporation, of New York, N.Y.

Other polyoxyethylene fatty alcohols which can be employed in accordance with the concepts of the present invention are polyoxyethylene (4) lauryl ether, polyoxyethylene (2) cetyl ether, polyoxyethylene (10) cetyl ether, polyoxyethylene (20) cetyl ether, polyoxyethylene (2) stearyl ether, polyoxyethylene (10) stearyl ether, polyoxyethylene (20) stearyl ether, polyoxyethylene (21) stearyl ether, polyoxyethylene (100) stearyl ether, polyoxyethylene (2) oleyl ether, polyoxyethylene (10) oleyl ether, and polyoxyethylene (20) oleyl ether.

Other suitable nonionic surfactants which are either ethoxylated alcohols or ethoxylated alkyl phenols are sold under the trademarks TERGITOL® and TRITON® by Union Carbide Corporation, Danbury, Conn.; NEODOL® by Shell Chemical Company, Houston, Tex.; MACOL® by PPG Industries, Gurnee, Ill.; and under the tradenames TRYCOL by Henkel Corporation, Ambler, Pa.; and BRIJ by ICI Americas Incorporated, Wilmington, Del.

In addition, some other types of nonionic surfactants which can be used are fatty acid alkanolamides or amine oxides. The fatty acid alkanolamides are nonionic surfactants obtained by reacting alkanolamines such as monoethanolamine, diethanolamine, monoisopropanolamine, or diisopropanolamine, with a fatty acid or fatty acid ester to form the amide. The hydrophobic portion of the nonionic surfactant is provided by a fatty acid hydrocarbon chain which generally has from ten to twenty-one carbon atoms. The fatty acid alkanolamide surfactants include fatty acid diethanolamides such as isostearic acid diethanolamide, lauric acid diethanolamide, capric acid diethanolamide, coconut fatty acid diethanolamide, linoleic acid diethanolamides, myristic acid diethanolamide, oleic acid diethanolamide, and stearic acid diethanolamide; fatty acid monoethanolamides such as coconut fatty acid monoethanolamide; and fatty acid monoisopropanolamides such as oleic acid monoisopropanolamide and lauric acid monoisopropanolamide. Representative of a suitable such nonionic surfactant is a product sold under the trademark WITCAMIDE® by Witco Corporation, New York, N.Y.

The amine oxides are nonionic surfactants obtained by oxidizing a tertiary amine to form the amine oxide. Amine oxide surfactants include the N-alkyl amine oxides such as N-cocodimethylamine oxide, N-lauryl dimethylamine oxide, N-myristyl dimethylamine oxide, and N-stearyl dimethylamine oxide; the N-acyl amine oxides such as N-cocamidopropyl dimethylamine oxide and N-tallowamidopropyl dimethylamine oxide; and N-alkoxyalkyl amine oxides such as bis(2-hydroxyethyl) $C_{12-15}$ alkoxypropylamine oxide. The hydrophobic portion of the amine oxide surfactants is generally provided by a fatty hydrocarbon chain containing from ten to twenty-one carbon atoms.

Representative amine oxide surfactants include lauric acid diethanolamide, N-lauryl dimethylamine oxide, coconut acid diethanolamide, myristic acid diethanolamide, and oleic acid diethanolamide- Suitable commercial materials are those products sold under tradenames and trademarks such as AMMONYX by the Stephan Company, Northfield, Ill.; BARLOX® by Lonza Incorporated, Fairlawn, N.J.; and MACKAMINE by The McIntyre Group Limited, University Park, Ill.

Sorbitan derivatives sold under the tradenames SPAN and TWEEN by ICI Americas Incorporated, Wilmington, Del.; and propylene oxide-ethylene oxide block polymers sold under the trademark PLURONIC® by BASF Corporation, Parsippany, N.J.; may also be employed.

The mixture also contains a cationic surfactant in addition to the nonionic surfactant. However, in an alternate embodiment of the invention, polymerization can be conducted with only the cationic surfactant.

Cationic surfactants which are useful in the invention include compounds which contain amino or quaternary ammonium hydrophilic moieties in the molecule and which are positively charged, such as quaternary ammonium salts. Representative quaternary ammonium salts which may be employed are ditallowdimethyl ammonium chloride, ditallowdimethyl ammonium methyl sulfate, dihexadecyl dimethyl ammonium chloride, di(hydrogenated tallow) dimethyl ammonium chloride, dioctadecyl dimethyl ammonium chloride, dieicosyl dimethyl ammonium chloride, didocosyl dimethyl ammonium chloride, di(hydrogenated tallow) dimethyl ammonium acetate, dihexadecyl dimethyl ammonium acetate, ditallow dipropyl ammonium phosphate, ditallow dimethyl ammonium nitrate, di(coconutalkyl) dimethyl ammonium chloride, and stearyl dimethyl benzyl ammonium chloride.

Suitable cationic surfactants are sold under tradenames or trademarks such as ADOGEN by Sherex Chemical Company Incorporated, Dublin, Ohio; EMCOL® by Witco Corporation, New York, N.Y.; TOMAH by Tomah Products Incorporated, Milton, Wis.; and ARQUAD and ETHOQUAD by Akzo Chemicals Incorporated, Chicago, Ill. One especially useful cationic surfactant according to this invention is an N-alkyl-trimethyl ammonium chloride sold under the tradename ARQUAD T-27W by Akzo.

The polymerization mixture which is used according to the invention preferably contains 50 to 80 percent by weight of water, 10 to 50 percent by weight of the cyclic siloxane, 5 to 15 percent by weight of the nonionic surfactant and the cationic surfactant, and 0.5 to 15 percent by weight of a silanolate or organosilanolate initiator.

The method of this invention is most preferably carried out by creating a mixture comprising a cyclic siloxane, a nonionic surfactant, a cationic surfactant, water, and the initiator; although as noted above, the method can also be carried out with only the cyclic siloxane, cationic surfactant, water, and the initiator. The mixture is then heated with agitation at a polymerization reaction temperature, until essentially all of the cyclic siloxane is reacted, and a stable oil-free emulsion is formed. The mixture of cyclic siloxane, nonionic surfactant, cationic surfactant, water, and initiator, is not stable and will separate without some means of agitation. Although it is not necessary to have all of the cyclic siloxane fully dispersed into the mixture during the reaction, some means of agitation must be provided throughout the course of the reaction.

Combining the cyclic siloxane, nonionic surfactant, cationic surfactant, water, and initiator, and then reacting the cyclic siloxanes to form the emulsion can take place in several ways. The first is to combine all of the ingredients with agitation, in any given order, and heat to the desired polymerization temperature with agitation, thereby allowing the cyclic siloxanes to react and form an emulsion. Another way is to combine all of the ingredients with agitation, except for the initiator, heat to the desired polymerization temperature, add the initiator, and thereafter heat and agitate at the desired polymerization temperature, thereby allowing the cyclic siloxanes to react and form an emulsion. Another way is to combine all of the ingredients with agitation, except for the cyclic siloxane, heat to the desired polymerization temperature, add or feed in the cyclic siloxane, and thereafter heat and agitate at the desired polymerization temperature, thereby allowing the cyclic siloxanes to react and form an emulsion.

It is not essential that the ingredients used in producing the emulsions by the method of this invention be combined in any given order. However, it is essential to have agitation during and following the addition of the ingredients, and to have achieved or to heat to the polymerization temperature, when all of the ingredients have been combined.

The preferred method for forming the emulsions is to create a mixture by combining the cyclic siloxane or mixture of cyclic siloxanes, preferably at least one nonionic surfactant, at least one cationic surfactant, and water; providing agitation such that the cyclic siloxane is fully dispersed in the mixture; heating to the polymerization temperature; and adding the initiator. The mixture is then held at the polymerization temperature with agitation until a stable oil-free emulsion is formed.

The method of this invention may also be carried out by combining and mechanically emulsifying at least the siloxane reactant, nonionic surfactant, cationic surfactant, and part of the water. Additional water, the initiator, and the surfactants can be added to the pre-emulsion with agitation. The mixture is then heated to the polymerization reaction temperature and held optionally with agitation, until the monomer is consumed in forming the emulsion.

Polymerization reaction temperatures useful in the method of the invention are typically above the freezing point and below the boiling point of water. Pressures above or below atmospheric pressure may allow operation outside of this range. The preferred temperature range is at least 50° C. but less than 95° C.

The polymerization reaction can be stopped at the desired level of conversion of cyclic siloxane and particle size, by using methods known in the art. It is preferred to stop the reaction when the largest amount of cyclic siloxane has been reacted, or when the ring-chain equilibrium for the system and the desired particle size have been obtained. Reaction times, typically of about three hours, are sufficient to achieve the desired particle size and level of conversion, according to this invention. The methods for stopping the reaction typically encompass neutralization of the initiator by the addition of an equal or slightly greater stoichiometric amount of acid. Either a strong or a weak acid may be used. Care must be taken when using a strong acid however not to over neutralize, as it may be possible to re-catalyze the reaction. It is preferred to neutralize with sufficient quantities of acid such that the resulting emulsion has a pH of about 7.

The following examples are set forth for the purpose of illustrating the invention in more detail.

EXAMPLE 1

Preparation of Saponified Aminosilane

The aminopropylmethyldisodium silanolate $H_2N(CH_2)_3Si(CH_3)(ONa)_2$ was prepared in a 500 ml glass flask by adding 80 grams (2 moles) of sodium hydroxide and 350 grams of deionized water, and mixing the contents until the sodium hydroxide dissolved. The contents of the flask were heated to 70° C., and 191 grams of aminopropylmethyldiethoxysilane (1 mole) was slowly added at a rate to maintain the temperature less than 80° C. while stirring. Ethanol was generated during the reaction and was removed by distillation.

EXAMPLE 2

Preparation of Saponified Dimethyldimethoxysilane

The disodium dimethylsilanolate $(CH_3)_2Si(ONa)_2$ was prepared in a 500 ml glass flask by adding 80 grams (2 moles) of sodium hydroxide and 250 grams of deionized water, and mixing the contents until the sodium hydroxide dissolved. The contents of the flask were heated to 70° C., and 120 grams of dimethyldimethoxysilane (1 mole) was added at a rate to maintain the temperature less than 80° C. with stirring. Methanol was generated during the reaction and was removed by distillation.

EXAMPLE 3—COMPARISON

Preparation of Control Emulsion

A Control emulsion was prepared for purposes of comparison with the emulsions produced according to the invention. The Control emulsion was prepared in a three-neck 1 liter flask by charging the flask with 337.5 grams of deionized water, 56.25 grams of Arquad T-27W cationic surfactant, 37.5 grams of Brij 35 Liquid nonionic surfactant, and 195 grams of octamethylcyclotetrasiloxane. The flask was heated to ninety degrees Centigrade. To the flask was added a preblend of 11.25 grams of aminopropylmethyldiethoxysilane (2 mole % amino), 22.5 grams of octamethylcyclotetrasiloxane, and 5.25 grams of a 14.3 % sodium hydroxide solution as the catalyst, instead of a silanolate. The mixture in the flask was stirred for 5–6 hours, and 1.125 grams of acetic acid, and 85 grams of additional deionized water, were added to neutralize the mixture. The mixture was cooled to room temperature and 5 ppm of a preservative was added. The product was a clear emulsion having a mean particle size of siloxane droplets of sixty-six nanometers (0.066 microns), as determined by measurement on a NICOMP Particle Size Analyzer. The viscosity of the siloxane polymer produced in accordance with the method of this comparison example was measured to be 1,900 centipoise (mPas) by solvent extraction of the siloxane from the emulsion water phase, and then removing the solvent prior to measurement on a Brookfield Viscometer.

ARQUAD T-27W is an N-alkyl-trimethyl ammonium chloride and the tradename of a product sold by Akzo Chemicals Incorporated, Chicago, Ill. BRIJ 35 Liquid is a tradename for a polyoxyethylene (23) lauryl ether having an HLB value of about 16.9, and a structure corresponding to $CH_{12}H_{25}(OCH_2CH_2)_{23}OH$. Laureth-23 is its CTFA adopted name, and this product is sold as a water solution containing 72 percent of the active ingredient, by ICI Americas Incorporated, Wilmington, Del.

EXAMPLE 4

Emulsion Preparation Using Saponified Aminosilane

Example 3 was repeated except that instead of using the aminopropylmethyldiethoxysilane, the aminopropylmethyldisodium silanolate $H_2N(CH_2)_3Si(CH_3)(ONa)_2$ prepared in Example 1 was utilized. In this example, the aminopropylmethyldisodium silanolate was added prior to the addition of octamethylcyclotetrasiloxane. The amount of aminopropylmethyldisodium silanolate used corresponded to 2 mole % amino functionality, which is the same level used in Example 3. After the mixture in the flask was stirred for 5 hours at 90° C., an acetic acid solution was added to neutralize the mixture. The mixture was cooled to room temperature and 5 ppm of a preservative was added. The product was a slightly hazy emulsion having a mean particle size of siloxane droplets of 78.6 nanometers (0.0786 microns), as determined by measurement on a NICOMP Particle Size Analyzer. The viscosity of the siloxane polymer produced could not be measured due to the limitations of the viscometer, but the viscosity was estimated to be greater than 1 million centipoise (mPas).

EXAMPLE 5

Emulsion Preparation Using Saponified Aminosilane

Example 3 was repeated except that instead of using the sodium hydroxide catalyst solution and aminopropylmethyldiethoxysilane, the aminopropylmethyldisodium silanolate $H_2N(CH_2)_3Si(CH_3)(ONa)_2$ prepared in Example 1 was utilized. The amount of aminopropylmethyldisodium silanolate used corresponded to 2 mole % amino functionality, which is the same level used in Example 3. In this example, the aminopropylmethyldisodium silanolate was added prior to the addition of octamethylcyclotetrasiloxane. The mixture in the flask was heated to 85° C. and stirred for 2.5 hours before being neutralized with an acetic acid solution. The mixture was cooled to room temperature and 5 ppm of a preservative was added. The product was a clear emulsion, with a very slight haze present, having a mean particle size of siloxane droplets of sixty-six nanometers (0.066 microns), as determined by measurement on a NICOMP Particle Size Analyzer. The viscosity of the siloxane polymer produced was measured to be 133,000 centipoise (mPas).

EXAMPLE 6

Emulsion Preparation Using Saponified Aminosilane

Example 5 was repeated except that instead of using 2 mole % aminopropylmethyldisodium silanolate, the level was reduced by half to 1 mole percent. The mixture was heated to 90° C. and stirred for 3 hours before being neutralized with an acetic acid solution. The product was a clear emulsion having a mean particle size of siloxane droplets of 52.9 nanometers (0.0529 microns), as determined by measurement on a NICOMP Particle Size Analyzer. The viscosity of the siloxane polymer produced was measured to be 81,000 centipoise (mPas).

EXAMPLE 7

Emulsion Preparation Using Saponified Aminosilane

Example 6 was repeated except that instead of using 2 mole % aminopropylmethyldisodium silanolate, the level was doubled to 4 mole percent. The mixture was heated to 85° C. and stirred for 2 hours before being neutralized with an acetic acid solution. The product was a slightly hazy emulsion having a mean particle size of siloxane droplets of 102.5 nanometers (0.1025 microns), as determined by measurement on a NICOMP Particle Size Analyzer. The viscosity of the siloxane polymer produced could not be measured due to the limitations of the viscometer, but the viscosity was estimated to be greater than 1 million centipoise (mPas).

EXAMPLE 8

Emulsion Preparation Using Saponified Dimethylsilane

Example 3 was repeated except that instead of using the sodium hydroxide catalyst solution and aminopropylmethyldiethoxysilane, the disodium dimethylsilanolate prepared in Example 2 was utilized. The amount of dimethylsilanolate used was 2 mole % based on the amount of actives, which is the same percent of an actives level as the aminosilane used in Example 3. In this example, the disodium dimethylsilanolate was added prior to the addition of octamethylcyclotetrasiloxane. The mixture in the flask was heated to 90° C. and stirred for 2.5 hours before being neutralized with an acetic acid solution. The mixture was cooled to room temperature and 5 ppm of a preservative was added. The product was a clear emulsion, with a very slight haze present, having a mean particle size of siloxane droplets of 47.6 nanometers (0.0476 microns), as determined by measurement on a NICOMP Particle Size Analyzer. The viscosity of the siloxane polymer produced was measured to be 1,670 centipoise (mPas).

EXAMPLE 9

Emulsion Preparation Using Saponified Dimethylsilane

Example 8 was repeated except that octamethylcyclotetrasiloxane was replaced with decamethylcyclopentasiloxane. The mixture in the flask was heated to 95° C. and stirred for 2.5 hours before being neutralized with an acetic acid solution. The mixture was cooled to room temperature and 5 ppm of a preservative was added. The product was a clear emulsion, with a very slight haze present, having a mean particle size of siloxane droplets of 79.9 nanometers (0.0799 microns), as determined by measurement on a NICOMP Particle Size Analyzer. The viscosity of the siloxane polymer produced was measured to be 1,700 centipoise (mPas).

With the advent of consumer trends toward daily hair washing, conditioning products such as shampoos have emerged which are designed to render the hair easy to comb and tangle free in the wet state, as well as glossy and soft when dry. Such conditioning is provided by cationic polymers, which upon rinsing, produce a thin film on the hair. The film functions as a lubricant when the hair is wet, and prevents static charge and "flyaway" when the hair is dry.

Conditioning may also be provided by hair conditioning products designed solely for that purpose, such as rinses, mousses, aerosols, and pump sprays. These conditioners are applied following shampooing. These conditioning products are rinsed from the hair a short time following their application. Such conditioners prevent excessive split ends and other mechanical hair damage and roughening, and seek to neutralize the adverse effects which hair undergoes due to humidity, temperature, exposure to sunlight, frequent washing, combing, and brushing, and cosmetic treatments such as bleaching, dyeing, and waving.

The emulsions produced by methods according to the invention were formulated into conditioning products in order to illustrate their utility in the personal care arena. The conditioning products of the invention were tested in accordance with standard industry techniques. In these tests, dark brown "virgin" European human hair was used for testing the conditioning efficacy of the products. A master hank of hair about eight inches in length was subdivided into a series of individual hair tresses. Each tress weighed about 2.5 grams. The top one inch portion of the hair tress was trimmed and glued to a 2"×2" (5.1×5.1 cm) plastic tab using DUCO CEMENT®. The cement was allowed to dry, and the hair tress was combed and trimmed to a length such that six inches of hair extended below the bottom of the plastic tab. Each "virgin" tress was rinsed for thirty seconds with forty degree Centigrade tap water. The tress was shampooed and lathered with two milliliters of a fifty percent solution of PRELL® shampoo for sixty seconds by stroking the tress downwardly. The tress was rinsed for sixty seconds with tap water. Excess water was removed from the tress by passing the tress between the index and middle fingers.

Instead of employing a commercial shampoo for treating the "virgin" tress, a cleaning solution can be prepared by combining 450 grams of distilled water with 450 grams of ammonium lauryl sulfate, which is an anionic surfactant sold under the tradename STANDAPOL A in the form of a liquid containing 30 percent of the active ingredient by Henkel Corporation, Ambler, Pa.

Following treatment of the tress, the tress is hand combed, and evaluated using the INSTRON "WET" and the INSTRON "DRY" COMBING procedures. INSTRON COMBING is an industry recognized test for determining hair conditioning by the ease of wet combing and the ease of dry combing. The test employs an INSTRON strain gauge which is equipped to measure the force required to comb the hair. Conditioning performance is based on the ability of a particular hair treating formulation such as a shampoo or a hair conditioner, to reduce the force required to comb the hair with the INSTRON strain gauge. The force is reported as Average Combing Load (ACL). The lower the (ACL) value, the better is the conditioning effect imparted by the formulation being evaluated. Typically, (ACL) base lines are initially established with "untreated" tresses. The Average Combing Load (ACL) is defined as the area under the force curve divided by the length or distance traveled by the INSTRON comb. This number is reported in grams or kilograms of force. The effectiveness of a treatment is the percent change in (ACL) after treatment, and this value is calculated as % Change ACL=treated hair ACL−untreated hair ACL×100 %/untreated ACL. An effective treatment is expressed as a negative number. A positive number indicates that treated hair is more difficult to comb than untreated hair.

For tests involving a conditioning shampoo, the hair tress is rinsed with tap water at 40° C. for thirty seconds. The test shampoo is applied to the tress in the amount of 0.5 milliliters, and lathered for thirty seconds by stroking the tress downwardly. The tress is rinsed for thirty seconds with 40° C. tap water, and 0.5 milliliters of the test shampoo are applied to the tress for a second time, and lathered for thirty seconds by stroking the tress downwardly. The tress is rinsed for thirty seconds with 40° C. tap water, and excess water is removed by passing the tress between the index and middle fingers.

For tests involving a hair conditioner, the hair tress is rinsed with tap water at 40° C. for thirty seconds. The test conditioner is applied to the tress in the amount of one milliliter, and the tress is stroked for thirty seconds. The tress is rinsed for thirty seconds with 40° C. tap water, and excess water is removed by passing the tress between the index and middle fingers.

According to the INSTRON WET COMBING method, each hair tress is soaked for 15–30 minutes in distilled water. Excess water is removed by passing the tress through the index and middle fingers. The tress is untangled by combing the tress by hand three times. The tress is retangled by dipping the tress in distilled water three times, and excess water is removed by passing the tress through the index and middle fingers twice. The tress is placed on a hanger and INSTRON combed.

According to the INSTRON DRY COMBING method, each hair tress is stored overnight in a constant environment to normalize the water content of the hair. The tress is untangled by combing the tress by hand three times. The tress is retangled by swirling the tress three times clockwise, and three times counter-clockwise. The tress is placed on a hanger and INSTRON combed.

The results of the INSTRON WET & DRY COMBING tests conducted with conditioning products according to this invention, and with comparison conditioning products, are shown below in the Tables.

TABLE I

| INSTRON WET COMBING | |
|---|---|
| Conditioner Applied | Percent Change (ACL) |
| Blank Conditioner | −11 |
| Silicone 1 | −62 |
| Silicone 2 | −74 |
| Silicone 3 | −80 |
| Silicone 4 | −73 |
| Silicone 5 | −79 |
| Commercial Silicone | −67 |

TABLE II

| INSTRON DRY COMBING | |
|---|---|
| Conditioner Applied | Percent Change (ACL) |
| Blank Conditioner | −34 |
| Silicone 1 | −48 |
| Silicone 2 | −56 |
| Silicone 3 | −65 |
| Silicone 4 | −67 |
| Silicone 5 | −70 |
| Commercial Silicone | −71 |

It can be seen from the above Tables, that the conditioners containing Silicones 1–5 which were the emulsions of the present invention, achieved a significantly better rating under both INSTRON Wet and Dry Combing tests; in comparison to a Blank Conditioner which was non-silicone containing. It can also be seen from the above Tables, that the conditioners containing Silicones 1–5, achieved a significantly better rating under the INSTRON Wet Combing test; with respect to the comparison conditioner containing a Commercial Silicone.

The conditioning products were further tested in a subjective evaluation with the aid of a panel of ten volunteers. The volunteers were each asked to test treated tresses by feeling the dry tress, and then by passing a comb through the tress. The volunteers assigned a number between one and five to each tress tested, with five being the tress which felt the best or was easiest to comb, and one being the tress which felt the worst or was the hardest to comb. Tables III and IV show the results of these subjective evaluations.

TABLE III

| SUBJECTIVE EVALUATION | |
|---|---|
| Conditioner Applied | DRY COMB |
| Silicone 1 | 2.5 |
| Silicone 2 | 1.7 |
| Silicone 3 | 2.5 |
| Silicone 4 | 1.4 |
| Silicone 5 | 1.5 |
| Commercial Silicone | 1.1 |

TABLE IV

| SUBJECTIVE EVALUATION | |
|---|---|
| Conditioner Applied | DRY FEEL |
| Silicone 1 | 2.2 |
| Silicone 2 | 2.7 |
| Silicone 3 | 2.2 |
| Silicone 4 | 1.7 |
| Silicone 5 | 1.9 |
| Commercial Silicone | 1.3 |

It can be seen from the above Tables, that the conditioners containing Silicones 1–5 which were the emulsions of the present invention, achieved a significantly better rating under both subjective tests; in comparison to the conditioner containing the Commercial Silicone.

The Commercial Silicone used to formulate the conditioner used for comparison in the above Tables, was an amine substituted siloxane polymer containing reactive silanol functionality ($\equiv$SiOH), stabilized in an aqueous emulsion by a cationic and a nonionic surfactant. This siloxane polymer has the formula $HO[(CH_3)_2SiO]_x[(OH)QSiO]_yH$ in which Q is $-CH_2CH_2CH_2NHCH_2CH_2NH_2$, and x and y are numbers depending on the molecular weight of the polymer. This polymer contains about 0.6 percent amine functionality, and has an initial viscosity of about two thousand Centistokes ($mm^2/s$) measured at twenty-five degrees Centigrade.

The Commercial Silicone polymer has been assigned the INCI name AMODIMETHICONE by The Cosmetic, Fragrance & Toiletry, Association (CTFA). It is described in numerous U.S. Patents, the most recent of which is U.S. Pat. No. 5,326,483, which issued Jul. 5, 1994. An emulsion form of the polymer is available commercially from the Dow Corning Corporation, Midland, Mich.

Silicone 1 in the Tables was a microemulsion produced according to the method of the present invention as shown in Example 4. The microemulsion contained 30 percent by weight of a silicone polymer having two mole percent of amine functionality in the molecule, an average particle diameter of 78.6 nanometers (0.0786 microns), and a viscosity in excess of one million Centistokes (mm$^2$/s).

Silicone 2 in the Tables was a microemulsion produced according to the method of the present invention as shown in Example 5. The microemulsion contained 30 percent by weight of a silicone polymer having two mole percent of amine functionality in the molecule, an average particle diameter of 66 nanometers (0.066 microns), and a viscosity of about 133,000 Centistokes (mm$^2$/s).

Silicone 3 in the Tables was a microemulsion produced according to the method of the present invention. The microemulsion contained 30 percent by weight of a silicone polymer having one mole percent of amine functionality in the molecule, an average particle diameter of 44 nanometers (0.044 microns), and a viscosity of about 21,100 Centistokes (mm$^2$/s).

Silicone 4 in the Tables was a microemulsion produced according to the method of the present invention as shown in Example 6. The microemulsion contained 30 percent by weight of a silicone polymer having one mole percent of amine functionality in the molecule, an average particle diameter of 52.9 nanometers (0.0529 microns), and a viscosity of about 81,000 Centistokes (mm$_2$/s).

Silicone 5 in the Tables was a microemulsion produced according to the method of the present invention as shown in Example 7. The microemulsion contained 30 percent by weight of a silicone polymer having four mole percent of amine functionality in the molecule, an average particle diameter of 102.5 nanometers (0.1025 microns), and a viscosity in excess of one million Centistokes (mm$^2$/s).

These silicone microemulsions of the invention are shown in the Table below as Nos. 1 to 5, respectively.

TABLE V

| No. | Weight Percent | Mole Percent Amine | Polymer Viscosity (cs) | Particle Size (nanometer) |
|---|---|---|---|---|
| 1 | 30 | 2 | >million | 78.6 |
| 2 | 30 | 2 | 133,000 | 66 |
| 3 | 30 | 1 | 21,100 | 44 |
| 4 | 30 | 1 | 81,000 | 52.9 |
| 5 | 30 | 4 | >million | 102.5 |
| 6 | 30 | 2 | 2,000 | 66 |

Silicone 6 in Table V was the microemulsion produced in Example 3 which is a method not according to the invention, and in which a silanolate or an organosilanolate was not used as the polymerization initiator. Under otherwise equivalent processing conditions however, it can be seen that the viscosity of the resulting polymer was much less than the viscosity of the polymers obtained by practicing the method of this invention. This demonstrates that the emulsion polymerization method of the invention enhances the rate of emulsion polymer formation, and that the method is capable of providing higher viscosity microemulsions in a shorter period of time than is possible with equivalent techniques known in the art.

The conditioner used in Tables I–IV to evaluate the various silicone emulsions contained 92 percent by weight of water, 1.5 percent by weight of a nonionic surfactant, one percent by weight of a thickener, three percent by weight of a consistency regulator and co-emulsifier for providing body and texture to the formulation, 0.5 percent by weight of a preservative, and sufficient of an acid for adjusting the pH. The Blank Conditioner contained no silicone. For the conditioners containing a silicone, two percent by weight of the water was replaced by a silicone emulsion.

The procedure for making these conditioners involved predispersing the thickener in about two-thirds of the water, and heating the predispersion to 75° Centigrade. The remaining one-third of the water was heated to 75° Centigrade and used to melt the nonionic surfactant and the co-emulsifier. The two portions of water were combined, subjected to high shear for about five minutes, and mixed for another five minutes. The mixture was cooled to forty degrees Centigrade, the silicone emulsion was added, and mixing was continued for ten more minutes. The mixture was allowed to cool to room temperature, the preservative was added, and the pH of the conditioner was adjusted with the acid.

The nonionic surfactant used to prepare these conditioners was an ethoxylated fatty alcohol sold under the tradename EUMULGIN B2 by Pulcra, S. A., of Barcelona, Spain. CETEARETH-20 is the CTFA INCI name for this polyoxyethylene (20) cetyl ether. This compound has the formula R(OCH$_2$CH$_2$)$_n$OH in which n is about twenty and R is a blend of alkyl groups derived from cetyl and stearyl alcohol.

The thickener used to prepare the conditioners was hydroxyethylcellulose which is sold under the tradename NATROSOL 250 HHR by Aqualon of Wilmington, Del. The consistency regulator and co-emulsifier was cetyl alcohol. The preservative was a mixture of diazolidinyl urea and parabens which is sold under the trademark GERMABEN® II-E by Sutton Laboratories of Chatham, N.J. Citric acid was used for adjusting the pH.

The details of the conditioner set forth above is not intended as limiting the present invention, but is merely provided for the purpose of illustrating the utility of invention as it relates to the hair care arena. The invention is applicable to any formulation intended to impart conditioning benefits to the hair, and can contain by way of example, 75–95 percent by weight of water, 1–40 percent by weight of one or more surfactants and co-emulsifiers, 1–3 percent by weight of a thickener, 0.1–1 percent by weight of a preservative, and 0.5–15 percent by weight of a silicone emulsion as one of the conditioning agents.

Thus, the hair conditioning compositions of the invention may contain other types of adjuvants than are enumerated above. For example, the composition may include adjuvants necessary to provide products which are aesthetically pleasant to the consumer, such as perfumes, colorants, electrolytes, foam boosters and builders, foam stabilizers, antimicrobials, antioxidants, ultraviolet light absorbers, pearlescent agents such as ethylene glycol monostearate and ethylene glycol distearate, and medicaments.

Thickeners used to facilitate the hand application of the composition to the hair, can be added in sufficient quantities to provide more luxurious effects. Other types of representative thickening agents which may be used are sodium alignate; gum arabic; guar gum; hydroxypropyl guar gum; cellulose derivatives such as methylcellulose, hydroxypropyl methylcellulose, and hydroxypropylcellulose; starch and starch derivatives such as hydroxyethylamylose and starch amylose; locust bean gum; electrolytes such as sodium chloride and ammonium chloride; saccharides such as fructose and glucose; and derivatives of saccharides such as PEG-120 methyl glucose dioleate.

Only cosmetically acceptable perfumes and fragrances should be used to prepare the composition. Colorants may be added where it is desired to confer a hue to the composition. Acids can be employed to adjust the pH within the range of about five to nine. Any water soluble carboxylic acid or mineral acid may be employed. Other suitable acidic compounds include mineral acids such as hydrochloric acid, sulfuric acid, and phosphoric acid; monocarboxylic acids such as acetic acid, lactic acid, and propionic acid; and polycarboxylic acids such as succinic acid, and adipic acid.

Additional organic cationic conditioning agents may be added to the composition for the purpose of providing more hair grooming benefit. Such organic cationic conditioning agents may include quaternary nitrogen derivatives of cellulose ethers; homopolymers of dimethyldiallyl ammonium chloride; copolymers of acrylamide and dimethyldiallyl ammonium chloride; homopolymers or copolymers derived from acrylic acid or methacrylic acid which contain cationic nitrogen functional groups attached to the polymer by ester or amide linkages; polycondensation products of N,N'-bis-(2,3-epoxypropyl)-piperazine or piperazine-bis-acrylamide and piperazine; and copolymers of vinylpyrrolidone and acrylic acid esters with quaternary nitrogen functionality. Specific materials include the various polyquats known under the INCI names of Polyquaternium-7, Polyquaternium-8, Polyquaternium-10, Polyquaternium-11, and Polyquaternium-23.

Cationic surfactants such as cetyl trimethylammonium chloride, cetyl trimethylammonium bromide, and stearyltrimethylammonium chloride, may also be employed in the compositions as the organic cationic conditioning agent.

Other types of preservatives may be required, and representative compounds which may be employed include formaldehyde, DMDM hydantoin, 5-bromo-5-nitro-1,3-dioxane, methyl paraben, propyl paraben, sorbic acid, imidazolidinyl urea, and 5-chloro-2-methyl-4-isothiazolin-3-one which is a product sold under the trademark KATHON® LX by the Rohm and Haas Company, Philadelphia, Pa.

The concept of the present invention is applicable to any hair care product intended to impart conditioning benefits to the hair, whether classified as a conditioner, a shampoo, or a so-called "two-in-one shampoo/conditioner" which both cleans and conditions.

The following examples are set forth for the purpose of illustrating in detail the alternate embodiment of the present invention, in which the nonionic surfactant is omitted. In this alternate method, a silicone emulsion is made by forming a mixture comprising water, a cyclic siloxane, and a cationic surfactant. There is added to the mixture a silanolate or organosilanolate polymerization initiator and the mixture is heated and agitated. The cyclic siloxane is then allowed to polymerize until an emulsion is formed. No nonionic surfactant is required during polymerization in accordance with this alternate embodiment, although a nonionic surfactant can be added after polymerization, in order to stabilize the emulsion which is formed.

EXAMPLE 10

Preparation of Sodium Saponified
Aminoethyl-Aminopropylmethyldimethoxysilane

The disodium aminoethylaminopropyl methylsilanolate $NH_2(CH_2)2NH(CH_2)3SiCH_3(ONa)_2$ was prepared in a 1000 milliliter glass flask by adding 80 grams (2 moles) of sodium hydroxide and 350 grams of deionized water, and mixing until the sodium hydroxide was dissolved. The contents of the flask was heated to 70° C., and 206 grams of aminoethyl-aminopropylmethyldimethoxysilane (1 mole) was added at a rate keeping the temperature less than 80° C. with stirring. Methanol generated during the reaction was removed by distillation. The percent non-volatile content was measured to be 51.6%.

EXAMPLE 11

Preparation of Potassium Saponified
Aminoethyl-Aminopropylmethyldimethoxysilane

The dipotassium aminoethylaminopropyl methylsilanolate $NH_2(CH_2)2NH(CH_2)3SiCH_3(OK)_2$ was prepared in a 1000 milliliter glass flask by adding 112.2 grams (2 moles; formula weight of 56.1 grams) of potassium hydroxide and 350 grams of deionized water, and mixing until the potassium hydroxide was dissolved. The contents of the flask was heated to 70° C., and 206 grams of aminoethyl-aminopropylmethyldimethoxysilane (1 mole) was added at a rate keeping the temperature less than 80° C. with stirring. Methanol generated during the reaction was removed by distillation. The percent non-volatile content was measured to be 51.66%.

EXAMPLE 12

Emulsion Preparation Using Sodium Saponified
Aminoethyl-Aminopropylmethyldimethoxysilane An emulsion was prepared by charging a flask with 402 grams of deionized water, 66 grams of ARQUAD T-27W, an N-alkyl trimethyl ammonium chloride cationic surfactant sold by Akzo Chemicals Incorporated, and 262.5 grams of a blend of dodecamethylcyclohexasiloxane, decamethylcyclopentasiloxane, and octamethylcyclotetrasiloxane. The contents of the flask were mixed for 20 minutes before processing the material through a homogenizer shear device using two passes at 7500 psi (51,711 kPa). The sheared material in the amount of 730.5 grams was added to a three-neck one liter flask, heated to 84° C. with stirring, and 9.46 grams of the disodium aminoethyl-aminopropyl methylsilanolate prepared in Example 10 was added. The contents of the flask were mixed at 84° C. for 8.75 hours before being cooled to 40° C., at which point the contents were neutralized with acetic acid to a pH of 7.0 to 7.5. Then 12.75 grams of a nonionic alkylphenoxypolyoxyethylene ethanol surfactant MAKON 10 sold by the Stephan Company of Northfield, Ill. was added to stabilize the emulsion. The product was a white emulsion having a mean particle size of siloxane droplets of 170.9 nanometers (0.1709 microns), as determined by measurement on a NICOMP Particle Size Analyzer. The viscosity of the siloxane polymer was measured to be 10,900 centistokes ($mm^2/s$) by solvent extraction of the siloxane from the emulsion water phase, and then removing the solvent prior to measurement on a Brookfield Viscometer.

EXAMPLE 13

Emulsion Preparation Using Potassium Saponified
Aminoethyl-Aminopropylmethyldimethoxysilane An emulsion was prepared by charging a flask with 402 grams of deionized water, 66 grams of ARQUAD T-27W an N-alkyl trimethyl ammonium chloride cationic surfactant sold by Akzo Chemicals Incorporated, and 262.5 grams of a blend of dodecamethylcyclohexasiloxane, decamethylcyclopentasiloxane, and octamethylcyclotetrasiloxane. The contents of the flask were mixed for 20 minutes before processing the material through a homogenizer shear device using two passes at 7500 psi (51,711 kPa). The sheared material in the amount of 730.5 grams was added to a three-neck one liter flask, heated to 84° C. with stirring, and 10.82 grams of the dipotassium aminoethyl-aminopropylmethylsilanolate prepared in Example 11 was added to the flask. The contents of the flask were mixed at 84° C. for 8.75 hours before cooling to 40° C., at which point the contents were neutralized with acetic acid to a pH of 7.0 to 7.5. Then 12.75 grams of a nonionic alkylphenoxypolyoxyethylene ethanol surfactant MAKON 10 sold by the Stephan Company of Northfield, Ill. was added to stabilize the emulsion. The product was a white emulsion having a mean particle size of siloxane droplets of 177.1 nanometers (0.1771 microns), as determined by measurement on a NICOMP Particle Size Analyzer. The viscosity of the siloxane polymer was measured to be 12,700 centistokes (mm2/s) by solvent extraction of the siloxane from the emulsion water phase, and then removing the solvent prior to measurement on a Brookfield Viscometer.

Surprisingly and quite unexpectedly, it has been found that silicone emulsions prepared according to the methods of the present invention, can provide an elastomeric product. Thus, the silicone emulsion produces an elastomeric product when water is removed under ambient conditions. When the silicone emulsion is spread out to form a coating, the water evaporates to leave a cured silicone elastomer. Heating the silicone emulsion can produce the elastomeric product, and other methods of removal of water other than evaporation can be employed, such as coagulation. Preferably however, films are prepared and cast from the silicone emulsions by spreading the silicone emulsion, and allowing the water to evaporate at room temperature. Such films find utility as coatings for substrates in order to impart to a substrate water repellent properties. Examples 14 and 15 are set forth below in order to illustrate this alternate embodiment of the invention.

EXAMPLE 14

Twenty-five grams of the emulsion prepared according to Example 4 were placed in a 100×15 millimeter standard polystyrene Petri dish and allowed to dry at room temperature for 72 hours. Upon removal of the water by evaporation, a one millimeter thick white film resulted. The whitish film was not sticky to the touch, and could be peeled cleanly away from the dish. This soft rubbery film was removed from the dish and was observed to have elastomeric characteristics, in that the film could be stretched slightly with full recovery upon release.

EXAMPLE 15

Twenty-five grams of the emulsion prepared according to Example 7 were placed in a 100×15 millimeter standard polystyrene Petri dish and allowed to dry at room temperature for 72 hours. Upon removal of the water by evaporation, a one millimeter thick white film resulted. The whitish film was not sticky to the touch, and could be peeled cleanly away from the dish. This soft rubbery film was removed from the dish and was observed to have elastomeric characteristics, in that the film could be stretched slightly with full recovery upon replease.

Other variations and modifications may be made in the compounds, compositions, and methods described herein, without departing from the essential features and concepts of the present invention.

The forms of the invention described herein are exemplary only, and are not intended as limitations on the scope of the invention as defined in the appended claims.

That which is claimed is:

1. A method of making a silicone emulsion including the steps of (i) forming a mixture comprising water, a cyclic siloxane, a nonionic surfactant, and a cationic surfactant; (ii) adding to the mixture a polymerization initiator which is a silanolate or an organosilanolate; (iii) heating the mixture; (iv) agitating the heated mixture; and (v) allowing the cyclic siloxane to polymerize until an emulsion is formed.

2. A method according to claim 1 in which the cyclic siloxane has the formula [—RR'Si—O—]$_n$ in which R and R' are selected from the group consisting of an alkyl radical having from one to six carbon atoms, an aryl radical, and an alkenyl radical; and n is an integer having a value of three to six.

3. A method according to claim 2 in which the polymerization initiator has the formula R''$_x$Si(OM)$_{4-x}$ in which R'' is selected from the group consisting of an alkyl radical having from one to six carbon atoms, an aryl radical, an alkenyl radical, an alkylamino radical, and an epoxy radical; x has a value of zero to three; and M is an alkali metal in Group IA of the Periodic Table.

4. A method according to claim 1 in which the polymerization initiator is a compound selected from the group consisting of sodium trimethylsilanolate NaOSi (CH$_3$)$_3$, sodium triphenylsilanolate (C$_6$H$_5$)$_3$SiONa, disodium dimethylsilanolate (CH$_3$)$_2$Si(ONa)$_2$, and disodium methylaminopropylsilanolate (CH$_3$)[NH$_2$CH$_2$CH$_2$CH$_2$]Si (ONa)$_2$.

5. A method according to claim 3 in which the nonionic surfactant is an ethoxylated alcohol selected from the group consisting of polyoxyethylene (4) lauryl ether, polyoxyethylene (23) lauryl ether, polyoxyethylene (2) cetyl ether, polyoxyethylene (10) cetyl ether, polyoxyethylene (20) cetyl ether, polyoxyethylene (2) stearyl ether, polyoxyethylene (10) stearyl ether, polyoxyethylene (20) stearyl ether, polyoxyethylene (21) stearyl ether, polyoxyethylene (100) stearyl ether, polyoxyethylene (2) oleyl ether, polyoxyethylene (10) oleyl ether, and polyoxyethylene (20) oleyl ether.

6. A method according to claim 1 in which the cationic surfactant is a quaternary ammonium salt selected from the group consisting of ditallowdimethyl ammonium chloride, ditallow dimethyl ammonium methyl sulfate, dihexadecyl dimethyl ammonium chloride, di(hydrogenated tallow) dimethyl ammonium chloride, dioctadecyl dimethyl ammonium chloride, dieicosyl dimethyl ammonium chloride, didocosyl dimethyl ammonium chloride, di(hydrogenated tallow) dimethyl ammonium acetate, dihexadecyl dimethyl ammonium acetate, ditallow dipropyl ammonium phosphate, ditallow dimethyl ammonium nitrate, di(coconutalkyl) dimethyl ammonium chloride, stearyl dimethyl benzyl ammonium chloride, and N-alkyl-trimethyl ammonium chlorides.

7. A method according to claim 3 in which the mixture is heated to a temperature within the range of 50° to less than 95° Centigrade, and the cyclic siloxane is allowed to polymerize for a period of time of less than five hours inclusive.

8. An emulsion prepared according to the method claimed in claim 1.

9. An emulsion prepared according to the method claimed in claim 1 in which the silicone in the emulsion has a particle size with an average diameter of less than 140 nanometers.

10. A method of conditioning hair comprising applying to hair an emulsion prepared according to the method claimed in claim 1.

11. In a hair conditioning composition which includes a silicone conditioning agent in an aqueous phase containing a surfactant, the improvement comprising the conditioning agent being an emulsion prepared according to the method claimed in claim 1.

12. A hair conditioning composition according to claim 11 in which the silicone has a particle size with an average diameter of less than 140 nanometers.

13. A hair conditioning composition according to claim 12 in which the emulsion is prepared by providing an amine functional silane in the mixture.

14. A method of making a silicone emulsion including the steps of (i) forming a mixture comprising water, a cyclic siloxane, and a cationic surfactant; (ii) adding to the mixture a polymerization initiator which is a silanolate or an organosilanolate; (iii) heating the mixture; (iv) agitating the heated mixture; and (v) allowing the cyclic siloxane to polymerize until an emulsion is formed.

15. A method according to claim 14 in which the cyclic siloxane has the formula $[-RR'Si-O-]_n$ in which R and R' are selected from the group consisting of an alkyl radical having from one to six carbon atoms, an aryl radical, and an alkenyl radical; and n is an integer having a value of three to six.

16. A method according to claim 14 in which the polymerization initiator has the formula $R'_xSi(OM)_{4-x}$ in which R" is selected from the group consisting of an alkyl radical having from one to six carbon atoms, an aryl radical, an alkenyl radical, an alkylamino radical, and an epoxy radical; x has a value of zero to three; and M is an alkali metal in Group IA of the Periodic Table.

17. A method according to claim 16 in which the polymerization initiator is a compound selected from the group consisting of sodium trimethylsilanolate $NaOSi(CH_3)_3$, sodium triphenylsilanolate $(C_6H_5)_3SiONa$, disodium dimethylsilanolate $(CH_3)_2Si(ONa)_2$, and disodium methylaminopropylsilanolate $(CH_3)[NH_2CH_2CH_2CH_2]Si(ONa)_2$.

18. A method of making a silicone microemulsion suitable to provide an elastomeric product upon removal of water under ambient conditions including the steps of (i) forming a mixture comprising water, a cyclic siloxane, a nonionic surfactant, and a cationic surfactant; (ii) adding to the mixture a polymerization initiator which is a silanolate or an organosilanolate; (iii) heating the mixture; (iv) agitating the heated mixture; (v) allowing the cyclic siloxane to polymerize until a microemulsion is formed; and (vi) removing the water from the microemulsion under ambient conditions.

19. An elastomeric product prepared according to the method in claim 18.

20. A method of making a silicone microemulsion suitable to provide an elastomeric product upon removal of water under ambient conditions including the steps of (i) forming a mixture comprising water, a cyclic siloxane, and a cationic surfactant; (ii) adding to the mixture a polymerization initiator which is a silanolate or an organosilanolate; (iii) heating the mixture; (iv) agitating the heated mixture; (v) allowing the cyclic siloxane to polymerize until a microemulsion is formed; and (vi) removing the water from the microemulsion under ambient conditions.

21. An elastomeric product prepared according to the method in claim 20.

* * * * *